United States Patent [19]

Browning

[11] Patent Number: 4,991,609
[45] Date of Patent: Feb. 12, 1991

[54] ULTRASONIC CLEANING METHOD AND APPARATUS

[76] Inventor: Iben Browning, 14 Guadin Loop, Sandia Park, N. Mex. 87047

[21] Appl. No.: 194,139

[22] Filed: May 16, 1988

[51] Int. Cl.$^5$ .............................................. B08B 3/10
[52] U.S. Cl. .................. 134/57 R; 134/105; 134/113; 134/111; 134/184
[58] Field of Search .................. 134/1, 184, 111, 57 R, 134/105, 113; 68/355

[56] References Cited

U.S. PATENT DOCUMENTS

| | | | |
|---|---|---|---|
| 2,650,872 | 9/1953 | Goldwasser | 68/355 X |
| 2,828,231 | 3/1958 | Henry | 68/355 |
| 3,348,556 | 10/1967 | Layton | 68/355 X |
| 3,871,395 | 3/1975 | Murry | 134/184 X |
| 3,873,071 | 3/1975 | Tatebe | 134/184 |
| 4,193,818 | 3/1980 | Young et al. | 134/184 X |
| 4,372,787 | 2/1983 | Fields et al. | 134/184 X |
| 4,561,902 | 12/1985 | Lee | 134/184 X |
| 4,697,605 | 10/1987 | Yung | 134/184 |

*Primary Examiner*—Frankie L. Stinson
*Attorney, Agent, or Firm*—Kokjer, Kircher, Bradley, Wharton, Bowman & Johnson

[57] ABSTRACT

The subject matter of the invention described herein is a cleaning device employing both ultrasonic and heat cleaning techniques and a method of cleaning an object utilizing techniques possible with the apparatus of the invention. The cleaning device includes a housing which receives a container for holding the object to be cleaned as well as a cleaning media. The housing defines a well which receives the container and the well is filled with water to partially surround the container. Heating elements raise the temperature of the cleaning media to at least 65° C. Independent means generate ultrasonic waves which are transmitted through the container wall to the object being cleaned. Sequential timing means first operates the ultrasonic wave generating means followed by the heating means. In this manner, particulate matter may be removed from the object to be cleaned by the ultrasonic waves including pulsating currents which are induced by the ultrasonic waves. The object is then pasteurized using heat without baking foreign particulate matter onto the object. The currents set up by the ultrasonic waves will also cause circulation within the container and appropriate filter means is utilized in the path of the currents to filter out foreign particulate matter. The method includes the steps of subjecting a cleaning media holding an object to be cleaned to ultrasonic waves over a period of time sufficient to loosen and remove solid material together with circulating cleaning media and filtering the circulating media to filter out loosed particles followed by heating of the cleaning media to pasteurization temperature.

14 Claims, 1 Drawing Sheet

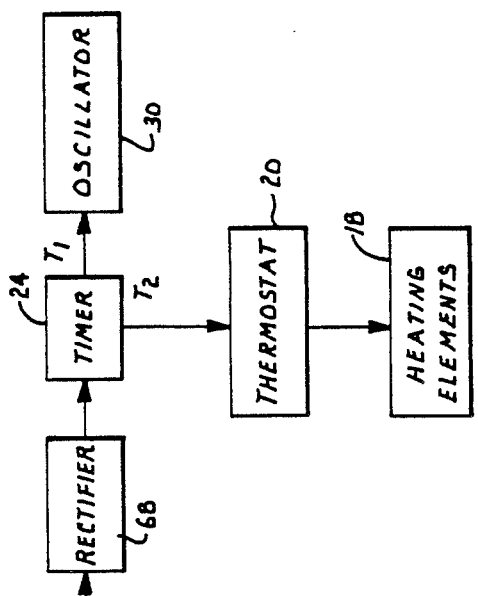
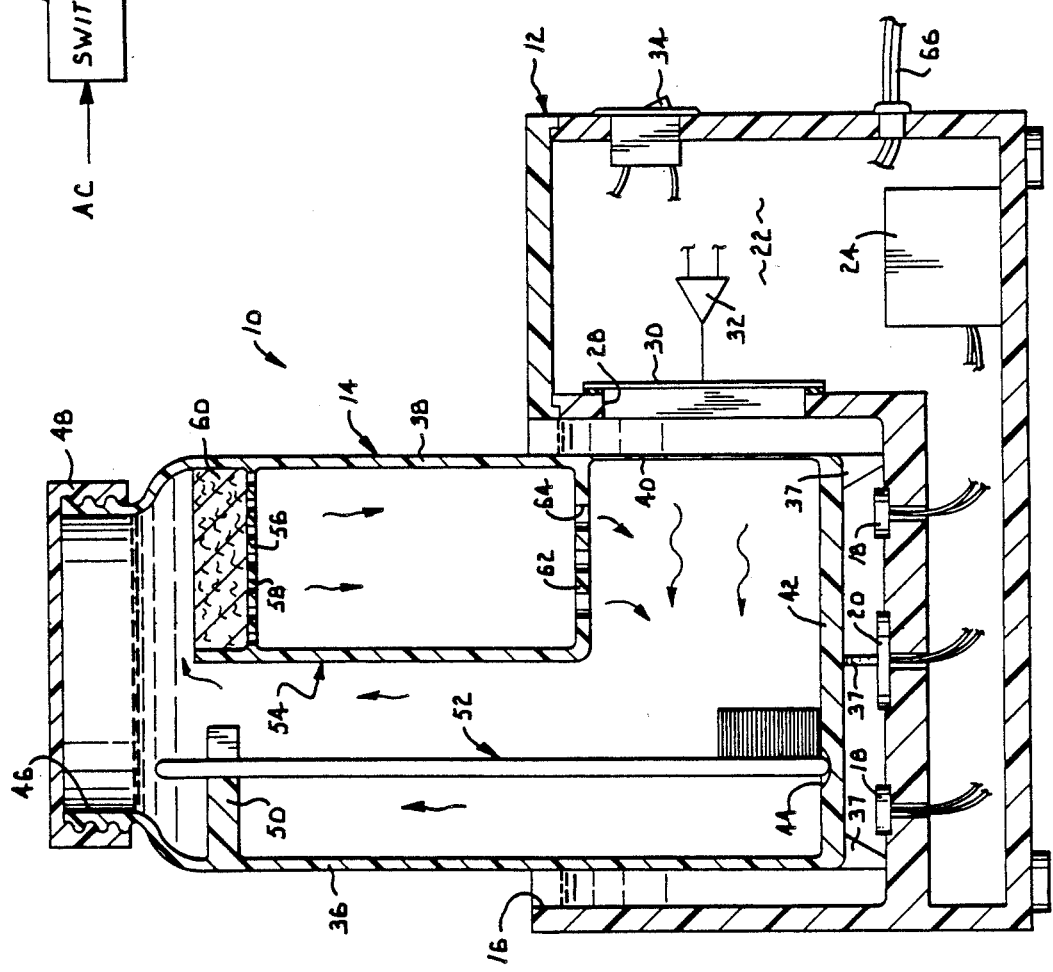

ULTRASONIC CLEANING METHOD AND APPARATUS

This invention relates generally to cleaning devices and, more particularly, to a method and apparatus for cleaning objects contaminated with solid foreign matter by utilizing both ultrasonic and heat energy sources.

Heat has long been utilized as one of the most effective and efficient means of cleaning, particularly with regard to objects to be used within the human body or animal bodies. Pasteurization is carried out at a temperature range of 65°–85° C. for a time period of at least 30 minutes.

It is also known to employ ultrasonic waves as an energy source for cleaning objects, particularly where solid matter is to be removed from an object. My prior Pat. No. 3,973,760 discloses ultrasonic cleaning and sterilizing apparatus particularly designed for contact lenses constructed of a hydrophilic copolymer. Other ultrasonic cleaning devices are disclosed by U.S. Pat. Nos. 3,595,532 and 4,114,194.

In the cleaning devices of the prior art where both heat and ultrasonic energy are utilized, there has been no attempt to sequence the institution of ultrasonic and heat energy sources. Instead, heat and ultrasonic waves are utilized simultaneously to effect the cleaning operation. This is acceptable where the object to be cleaned is not subject to foreign matter building up on the object or where the elevated temperature is maintained low enough that there is no tendency to bake the foreign matter onto the object being cleaned. In the case of certain objects such as toothbrushes, there is a considerable tendency for solid foreign matter to build up on the object. This foreign matter can effectively be removed utilizing ultrasonic energy. Because of the need to pasteurize the toothbrush, it is necessary to elevate the temperature to a range of about 65°–85° C. which is high enough to cause some foreign matter to bake onto the toothbrush. Thus, if ultrasonic waves and sufficient heat to pasteurize are applied simultaneously to an object such as a toothbrush, the object will be sterilized but it will also have substantial foreign matter remaining on the object after cleaning, and because of the baking process this foreign matter will be more difficult to remove than prior to the cleaning operation.

It is, therefore, a primary object of the present invention to provide a method and apparatus for the aqueous cleaning of objects such as toothbrushes and the like which utilize both ultrasonic waves and pasteurization in a sequenced manner to minimize the buildup of foreign deposits while sterilizing the object being cleaned.

Another one of the objects of my invention is to provide a method and apparatus for the aqueous cleaning of objects such as toothbrushes and the like wherein heat, ultrasonic waves, water current and filtration are all utilized in timed sequence to maximize the cleaning operation.

As a corollary to the foregoing object, it is an aim of the invention to provide a method and apparatus of the type stated wherein the filtration is effected by a removable filter element which can be taken out and cleaned to lengthen its useful life.

Another one of the objectives of this invention is to provide a method and apparatus for cleaning objects such as toothbrushes and the like wherein heat, ultrasonic waves, water current and filtration are all utilized to effect cleaning and the ultrasonic waves are used to induce circulation in the cleaning media thereby enhancing the effectiveness of the filtration feature.

It is an object of the invention to provide a method and apparatus of the type referred to in the preceding paragraphs wherein the apparatus incorporates a switching mechanism for automatic off-on operation.

Another one of the aims of the invention is to provide a method and apparatus of the type described in the foregoing aims and objects which is small enough to be portable so that it can be moved to different locations by the user.

Still another object of my invention is to provide a method and apparatus which meets the aims and objects heretofore set forth and can also be designed to operate on either AC or DC current.

Other objects of the invention will be made clear or become apparent from the following description and claims when read in light of the accompanying drawing wherein:

FIG. 1 is a vertical cross-sectional view of the device according to the present invention; and FIG. 2 is a schematic illustration of the circuitry employed in the device of FIG. 1.

Referring initially to FIG. 1, the cleaning device of the present invention is designated generally by the numeral 10 and includes a housing 12 and a container 14 received by the housing.

Referring initially to details of housing 12, the housing will normally be formed from a molded plastic or other suitable material and includes a shallow well 16 which is water-tight and receives container 14. A plurality of heating elements 18 are fixed to the bottom of well 16 along with a heat sensing element 20.

That portion of housing 12 which is not utilized for well 16 presents an open area 22. Disposed within open area 22 is a timer 24. An opening 28 is provided in a sidewall of housing 12 which defines well 16. Placed over opening 28 in sealing relationship to the housing is a tuning element 30 which is electrically coupled with a transducer element 32 which is preferably a piezoelectric ceramic crystal, although other suitable transducer mechanisms may be employed. A master switch 34 is also mounted on one of the exterior walls of housing 12 and is operable by a user of the device.

Referring now to details of container 14, the container is generally cylindrically shaped having a first sidewall 36 of uniform width, a second sidewall 38 which forms a thin membrane 40 as it approaches the container bottom 42. Bottom 42 has a recessed portion 44 for purposes to be made clear hereinafter. Container 14 has an open top 46 which is closed by a removable lid 48 that is threadably received by the uppermost portions of sidewalls 36 and 38. Container 14 is preferably constructed from molded plastic and includes, interiorally of the container, an arm 50 which holds a toothbrush 52 the brush end of which is received in recess 44.

Also integrally molded with container 14 is an interior compartment 54 which includes a shelf 56 having a plurality of through openings 58. Shelf 56 is positioned below the top of compartment 54 so that the sidewall of the compartment serves to assist in retaining a filter pad 60 on top of the shelf in overlying relationship to openings 58. A bottom wall 62 of compartment 54 is spaced downwardly from shelf 56 and is also provided with a plurality of through openings 64.

Referring additionally to FIG. 2, an AC power source provides current to the oscillator 30, heating elements 18, sensor 20 and timer 24 through a supply line 66. The supply line is interrupted by switch 34 which is connected with a rectifier 68 for rectifying the AC signal. The signal from rectifier 68 is delivered to timer 24 which produces two output signals T1 and T2 which are transmitted to oscillator 30 through transducer 32 and appropriate connecting lines and to heat sensing thermostat 20 which in turn has its output connected to heating elements 18.

Timer 24 is programmed to provide a first output signal T1 to oscillator 30 for a period of approximately one-half to one hour during which time there is no signal to thermostat 20 and heating elements 18 are inactive. At the end of the oscillator cycle, a second signal T2 to thermostat 20 activates heating elements 18 which will remain activated for an additional period of one-half to one hour at a preselected temperature preferably at least 65° C. and normally within the range of 65°-85° C. At the end of the second timing cycle, the device will automatically shut off until switch 34 is reset.

In use, container 14 is filled with an aqueous cleaning media which may be tap water or in some instances tap water with a small amount of salt, mouthwash, or other cleaning agent or disinfectant added. Toothbrush 52 is placed in the container where it is held by arm 50 in an upright position. Lid 48 is then securely threaded onto the container and the container placed in well 16 where it is held in spaced relationship to the bottom of the well by feet 37.

Well 16 is filled with water to a height at least equal to the distance membrane 40 extends above the bottom of the well. Upon turning on switch 34, oscillator will generate ultrasonic waves within the range of 30-100 kHz, preferably about 40 kHz. These ultrasonic waves will pass through the water in well 16 and also through membrane 40 and then resonate through the body of water in container 14. The presence of water in well 16 as well a the utilization of a thin membrane wall 40 for container 14 are very advantageous in minimizing attenuation of the waves as they leave the oscillator and enter the container. The result will be pulsating currents of water which strike the bristles of brush 52 so as to separate solid foreign particles which may have accumulated on the brush. These currents will then be deflected off of sidewall 36 upwardly toward the top of the container where they will turn and be directed through filter pad 60 and interior separating compartment 54. A significant percentage of the total particulate material removed from toothbrush 52 will be trapped within filter pad 60. The water passing through the filter pad will emanate from the interior compartment through openings 64 which will have a tendency to accelerate the velocity of the fluid because of the limited number of openings. This will further enhance circulation of water within the container.

As previously indicated, after oscillator 30 has operated for a period of one-half to one hour, thermostat 20 will activate heating elements 18 which will heat the water in well 16 which then in turn heats the water in container 14. Elements 18 are preferably selected so as to be capable of raising the temperature in the container to a range of 65°-85° C., preferably about 70° C. The thermostatic sensor 20 will monitor the temperature to cycle the heating elements 18 on and off so as to maintain this temperature. Manifestly, the temperature should be maintained at the level indicated for a period of one-half to one hour so as to effect pasteurization of the toothbrush 52. Those skilled in the art will recognize that it is within the scope of the invention to provide an adjustable thermostat so that the temperature to which the liquid in container 14 is raised may be varied as needed. It is also likely that an indicator light will be included in the control circuitry for the device so as to provide a visual indicator whenever the device is turned on and, if desirable, a second indicator light when heating elements 18 are in operation.

The combined effect of sequentially operating oscillator 30 to generate ultrasonic cleaning waves in timed sequence with pasteurization heat provides a cleaning method having superior results to those heretofore known. The additive effect of the pulsating water currents and filtration of removed particulate matter further enhances the effectiveness of the device according to the present invention.

Once cleaning is completed, the device will automatically cycle to an off stage and toothbrush 52 can be removed for use. When an accumulation of particulate matter on filter pad 60 necessitates it, the pad may be removed and the accumulated material washed from the pad which is then reinserted into the container. It may also be desirable in some instances to provide a sensor element in recess 44 so that the device is automatically activated whenever a toothbrush 52 is placed into the position indicated in the drawing.

I claim:

1. A cleaning device for use with an aqueous cleaning media in cleaning objects placed in the media, said device comprising:
   a housing adapted to receive a container for holding said cleaning media and an object to be cleaned;
   means in said housing for heating said cleaning media to a temperature of at least 65° C.;
   means in said housing for sensing the temperature of said media in said container, said temperature sensing means being coupled with said heating means;
   means in said housing for generating ultrasonic waves in said media; and
   timing means coupled with both said ultrasonic wave generating means and said heating means and operable to provide sequential activation of said wave generating means and said heating means, the activation of said heating means following the activation of said wave generating means.

2. The invention of claim 1, wherein said housing is adapted to hold a quantity of water sufficient to surround a portion of said container.

3. The invention of claim 2, wherein said heating means is characterized by an ability to heat said media in said container to a temperature of a least 65° C. for at least 30 minutes.

4. The invention of claim 2, wherein said ultrasonic wave generating means is characterized by an ability to generate waves of about 30 to 100 kHz.

5. The invention of claim 4, wherein said heating means is characterized by an ability to heat said media in said container to a temperature of at least 65° C. for at least 30 minutes.

6. The invention of claim 5, wherein said device includes means for sensing the temperature of said media in said container, said temperature sensing means being coupled with said heating means and providing a signal for controlling operation of said heating means.

7. A device for cleaning objects in an aqueous cleaning media, said device comprising:
   a housing;

a container adapted to receive said object and an aqueous cleaning media, said container being further adapted to be received by said housing;

said housing being adapted to receive a quantity of water for partially surrounding said container;

means in said housing for heating said cleaning media to a temperature of at least 65° C.;

means in said housing for sensing the temperature of said media in said container, said temperature sensing means being coupled with said heating means;

means in said housing for generating ultrasonic waves in said media, said ultrasonic wave generating means being positioned below the level of water surrounding said container; and timing means coupled with both said ultrasonic wave generating means and said heating means and operable to provide sequential activation of said wave generating means and said heating means, the activation of said heating means following the activation of said wave generating means.

8. A device as set forth in claim 7, wherein said container is characterized by at least one wall of a thickness to accommodate the passage of ultrasonic waves therethrough.

9. A device as set forth in claim 8, wherein said container includes a filtration chamber for said cleaning media.

10. A device as set forth in claim 9, wherein said filtration chamber includes removable filter means.

11. The invention of claim 8, wherein said heating means is characterized by an ability to heat said media in said container to a temperature of at least 65° C. for at least 30 minutes.

12. The invention of claim 8, wherein said ultrasonic wave generating means is characterized by an ability to generate waves of about 30 to 100 kHz.

13. The invention of claim 12, wherein said heating means is characterized by an ability to heat said media in said container to a temperature of at least 65° C. for at least 30 minutes.

14. The invention of claim 13, wherein said device includes means for sensing the temperature of said media in said container, said temperature sensing means being coupled with said heating means and providing a signal for controlling operation of said heating means.

* * * * *